(12) United States Patent
Bergsma et al.

(10) Patent No.: US 6,294,364 B1
(45) Date of Patent: *Sep. 25, 2001

(54) HUMAN FAS

(75) Inventors: Derk J Bergsma, Berwyn, PA (US); Conrad Chapman, Orpington (GB); Megan E Depiera, Haverford, PA (US); Catherine E Ellis, Glassboro, NJ (US); John Lonsdale, Exton; Jeffrey L Mooney, Limerick, both of PA (US)

(73) Assignee: SmithKline Beecham Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/261,907

(22) Filed: Mar. 3, 1999

(51) Int. Cl.⁷ ............................ C12N 15/52; C12N 15/85; C07H 21/04
(52) U.S. Cl. .................. 435/183; 435/252.3; 435/320.1; 435/325; 536/23.1; 536/23.2; 536/23.5
(58) Field of Search ................................. 536/23.1, 24.5, 536/23.5, 23.2; 435/320.1, 69.1, 252.3, 325, 177, 183; 514/44

(56) References Cited

U.S. PATENT DOCUMENTS 5,665,874 * 9/1997 Kuhajda et al. ................... 536/24.3

OTHER PUBLICATIONS

Kuhajda et al. Accession No. T88206, Jan. 1998.*
Kuhajda et al. Accession No. I64893, Sep. 1997.*
Hennnigar et al. Accession No. U29344, Aug. 1995.*
Jayakumar et al. Accession No. U26644, Nov. 1995.*
Amy et al. Accession No. P12785, Oct. 1989.*
Amy et al. Accession No. Q63577, Nov. 1996.*
Jayakumar et al. Accession No. P49327, Nov. 1996.*
Henniger et al. Accession No. Q16702, Nov. 1996.*
Leube et al. Journal of Cell Biology. 127(6): 1589–1601, Dec. 1994.*
Ledley, F.D. Pharmaceutical Research. 13: 1595–1613, Nov. 1996.*
Branch, A.D. TIBS 23: 45–50, Feb. 1998.*
Verma et al. Nature. 389: 239–242, Sep. 1997.*
Milgraum et al. Clin Cancer Res. 3(11): 2115–20, Nov. 1997.*
Jakakumar et al. Proc. Natl Academy Sciences. 92: 8695–8699, Sep. 1995.*
Jayakumar et al., "Human fatty acid synthase: Prpoerties and molecular cloning", PNAS USA, Vol. 92(19) pp. 8695–8699 (1995).
GenBank Accession No. U29344, Aug. 1995.
GenBank Accession No. G01880; Jenna et al., Jun. 6, 1997.*
GenBank Accession No. A57788; Jayakumar et al., Jul. 10, 1998.*
GenBank Accession No. A30313; Amy et al., Sep. 30, 1991.*
GenBank Accession No. W32881; Kuhajda et al., Jan. 16, 1998.*
Jayakumar, et al., "Cloning and expression of the multifunctional human fatty acid synthase and its subdomains in *Escherichia coli*", Proc. Natl. Acad. Sci. USA, vol. 93, pp. 14509–14514 (1966).
Jayakumar, et al., "Human fatty acid synthase: Assembling recombinant halves of the fatty acid synthase subunit protein reconstitutes enzyme activity", Proc. Natl. Acad. Sci. USA, vol. 94, pp. 12326–12330 (1997).
Chirala, et al., "Animal fatty acid synthase: Functional mapping and cloning and expression of the domain I constituent activities", Proc. Natl. Acad. Sci. USA, Vo. 94, pp. 5588–5593 (1997).

* cited by examiner

Primary Examiner—John L. LeGuyader
Assistant Examiner—Shin-Lin Chen
(74) Attorney, Agent, or Firm—Elizabeth J. Hecht; Ratner & Prestia; William T. King

(57) ABSTRACT

Fatty Acid Synthase polypeptides and polynucleotides and methods for producing such polypeptides by recombinant techniques are disclosed. Also disclosed are methods for utilising Fatty Acid Synthase polypeptides and polynucleotides in therapy, and diagnostic assays for such.

13 Claims, No Drawings

SEQUENCE LISTING

<160> NUMBER OF SEQ ID NOS: 2

<210> SEQ ID NO 1
<211> LENGTH: 8519
<212> TYPE: DNA
<213> ORGANISM: HOMO SAPIENS

<400> SEQUENCE: 1

```
gtcgacccac gcgtccgccc acgcgtccgc ccacgcgtcc ggctccgccg cgctccagcc      60
tcgctctccg ccgcccgcac cgccgcccgc gccctcacca gggatggcct gggacaagct     120
ccaggagcct tggaaggctg agactcagag cagccatgga ggaggtggtg attgccggca     180
tgtccgggaa gctgccagag tcggagaact tgcaggagtt ctgggacaac ctcatcggcg     240
gtgtggacat ggtcacggac gatgaccgtc gctggaaggc ggggctctac ggcctgcccc     300
ggcggtccgg caagctgaag gacctgtcta ggtttgatgc ctccttcttc ggagtccacc     360
ccaagcaggc acacacgatg gaccctcagc tgcggctgct gctggaagtc acctatgaag     420
ccatcgtgga cggaggcatc aacccagatt cactccgagg aacacacact ggcgtctggg     480
tgggcgtgag cggctctgag acctcggagg ccctgagccg agaccccgag acactcgtgg     540
gctacagcat ggtgggctgc cagcgagcga tgatggccaa ccggctctcc ttcttcttcg     600
acttcagagg gccagcatc gcactggaca cagcctgctc ctccagcctg atggcc ctgc     660
agaacgccta ccaggccatc acagcgggc agtgccctgc cgccatcgtg ggggcatca      720
acgtcctgct gaagcccaac acctccgtgc agttcttgag gctggggatg ctcagccccg     780
agggcacctg caaggccttc gacacagcgg ggaatgggta ctgccgctcg gagggtgtgg     840
tggccgtcct gctgaccaag aagtccctgg cccggcgggt gtacgccacc atcctgaacg     900
ccggcaccaa tacagatggc ttcaaggagc aaggcgtgac cttcccctca ggggatatcc     960
aggagcagct catccgctcg ttgtaccagt cggccggagt ggcccctgag tcatttgaat    1020
acatcgaagc ccacggcaca ggcaccaagg tgggcgaccc ccaggagctg aatggcatca    1080
cccgagccct gtgcgccacc cgccaggagc cgctgctcat cggctccacc aagtccaaca    1140
tggggcaccc ggagccagcc tcggggctgg cagccctggc caaggtgctg ctgtccctgg    1200
agcacgggct ctgggccccc aacctgcact ccatagccc caaccctgag atcccagcgc    1260
tgttggatgg gcggctgcag gtggtggacc agccctgcc cgtccgtggc ggcaacgtgg    1320
gcatcaactc ctttggcttc ggggctcca acgtgcacat catcctgagg cccaacacgc    1380
agccgccccc cgcacccgcc ccacatgcca ccctgcccc tctgctgcgg gccagcggac    1440
gcaccctga ggccgtgcag aagctgctgg agcagggcct ccggcacagc caggacctgg    1500
ctttcctgag catgctgaac gacatcgcg ctgtccccgc caccgccatg cccttccgtg     1560
gctacgctgt gctgggtggt gagcgcggtg cccagaggt gcagcaggtg cccgctggcg    1620
agcgcccgct ctggttcatc tgctctggga tgggcacaca gtggcgcggg atggggctga    1680
gcctcatgcg cctggaccgc ttccgagatt ccatcctacg ctccgatgag gctgtgaagc    1740
cattcggcct gaaggtgtca cagctgctgc tgagcacaga cgagagcacc tttgatgaca    1800
tcgtccattc gtttgtgagc ctgactgcca tccagatagg cctcatagac ctgctgagct    1860
gcatggggct gaggccagat ggcatcgtcg ccactccct gggggaggtg gcctgtggct    1920
acgccgacgg ctgcctgtcc caggaggagg ccgtcctcgc tgcctactgg aggggacagt    1980
gcatcaaaga agcccatctc ccgccgggcg ccatggcagc cgtgggcttg tcctgggagg    2040
```

| | |
|---|---|
| agtgtaaaca gcgctgcccc ccgggcgtgg tgcccgcctg ccacaactcc aaggacacag | 2100 |
| tcaccatctc gggacctcag gccccggtgt ttgagttcgt ggagcagctg aggaaggagg | 2160 |
| gtgtgtttgc caaggaggtg cggaccggcg gtatggcctt ccactcctac ttcatggagg | 2220 |
| ccatcgcacc cccactgctg caggagctca agaaggtgat ccgggagccg aagccacgtt | 2280 |
| cagcccgctg gctcagcacc tctatccccg aggcccagtg gcacagcagc ctggcacgca | 2340 |
| cgtcctccgc cgagtacaat gtcaacaacc tggtgagccc tgtgctgttc caggaggccc | 2400 |
| tgtggcacgt gcctgagcac gcggtggtgc tggagatcgc gccccacgcc ctgctgcagg | 2460 |
| ctgtcctgaa gcgtggcctg aagccgagct gcaccatcat ccccctgatg aagaaggatc | 2520 |
| acagggacaa cctggagttc ttcctggccg gcatcggcag gctgcacctc tcaggcatcg | 2580 |
| acgccaaccc caatgccttg ttcccacctg tggagttccc agctccccga ggaactcccc | 2640 |
| tcatctcccc actcatcaag tgggaccaca gcctggcctg ggacgtgccg gccgccgagg | 2700 |
| acttccccaa cggttcaggt tccccctcag ccgccatcta caacatcgac accagctccg | 2760 |
| agtctcctga ccactacctg gtggaccaca ccctcgacgg tcgcgtcctc ttccccgcca | 2820 |
| ctggctacct gagcatagtg tggaagacgc tggcccgcgc cctgggcctg ggcgtcgagc | 2880 |
| agctgcctgt ggtgtttgag gatgtggtgc tgcaccaggc caccatcctg cccaagactg | 2940 |
| ggacagtgtc cctggaggta cggctcctgg aggcctcccg tgccttcgag gtgtcagaga | 3000 |
| acggcaacct ggtagtgagt gggaaggtgt accagtggga tgaccctgac ccaggctct | 3060 |
| tcgaccaccc ggaaagcccc accccaaccc cacggagcc cctcttcctg cccaggctg | 3120 |
| aagtttacaa ggagctgcgt ctgcgtggct acgactacgg ccctcatttc cagggcatcc | 3180 |
| tggaggccag cctggaaggt gactcgggga ggctgctgtg gaaggataac tgggtgagct | 3240 |
| tcatggacac catgctgcag atgtccatcc tgggctcggc caagcacggc ctgtacctgc | 3300 |
| ccacccgtgt caccgccatc cacatcgacc ctgccaccca caggcagaag ctgtacacac | 3360 |
| tgcaggacaa ggcccaagtg gctgacgtgg tggtgagcag gtggctgagg gtcacagtgg | 3420 |
| ccggaggcgt ccacatctcc gggctccaca ctgagtcggc cccgcggcgg cagcaggagc | 3480 |
| agcaggtgcc catcctggag aagttttgct tcactcccca cacggaggag gggtgcctgt | 3540 |
| ctgagcgcgc tgccctgcag gaggagctgc aactgtgcaa ggggctggtg caggcactgc | 3600 |
| agaccaaggt gacccagcag gggctgaaga tggtggtgcc cggactggat ggggcccaga | 3660 |
| tcccccggga cccctcacag caggaactgc cccggctgtt gtcggctgcc tgcaggcttc | 3720 |
| agctcaacgg gaacctgcag ctggagctgg cgcaggtgct ggcccaggag aggcccaagc | 3780 |
| tgccagagga ccctctgctc agcggtctcc tggactcccc ggcactcaag gcctgcctgg | 3840 |
| acactgccgt ggagaacatg cccagcctga agatgaaggt ggtggaggtg ctggctggcc | 3900 |
| acggtcacct gtattcccgc atcccaggcc tgctcagccc ccatcccctg ctgcagctga | 3960 |
| gctacacggc caccgaccgc cacccccagg ccctggaggc tgcccaggcc gagctgcagc | 4020 |
| agcacgacgt tgcccagggc cagtgggatc ccgcagaccc tgcccccagc gccctgggca | 4080 |
| gcgccgacct cctggtgtgc aactgtgctg tggctgccct cggggacccg gcctcagctc | 4140 |
| tcagcaacat ggtggctgcc ctgagagaag ggggctttct gctcctgcac acactgctcc | 4200 |
| gggggcaccc cctcggggac atcgtggcct tcctcacctc cactgagccg cagtatggcc | 4260 |
| agggcatcct gagccaggac gcgtgggaga gcctcttctc cagggtgtcg ctgcgcctgg | 4320 |
| tgggcctgaa gaagtccttc tacggctcca cgctcttcct gtgccgccgg cccacccgc | 4380 |
| aggacagccc catcttcctg ccggtggacg ataccagctt ccgctgggtg gagtctctga | 4440 |

-continued

```
agggcatcct ggctgacgaa gactcttccc ggcctgtgtg gctgaaggcc atcaactgtg   4500
ccacctcggg cgtggtgggc ttggtgaact gtctccgccg agagcccggc gggaaccgcc   4560
tccggtgtgt gctgctctcc aacctcagca gcacctccca cgtcccggag gtggacccgg   4620
gctccgcaga actgcagaag gtgttgcagg agacctggt gatgaacgtc taccgcgacg    4680
gggcctgggg ggctttccgc cacttcctgc tggaggagga caagcctgag gagccgacgg   4740
cacatgcctt tgtgagcacc ctcacccggg gggacctgtc ctccatccgc tgggtctgct   4800
cctcgctgcg ccatgcccag cccacctgcc ctggcgccca gctctgcacg gtctactacg   4860
cctccctcaa cttccgcgac atcatgctgg ccactggcaa gctgtcccct gatgccatcc   4920
cagggaagtg gacctcccag gacagcctgc taggtatgga gttctcgggc cgagacgcca   4980
gcggcaagcg tgtgatggga ctggtgcctg ccaagggcct ggccacctct gtcctgctgt   5040
caccggactt cctctgggat gtgccttcca actggacgct ggaggaggcg gcctcggtgc   5100
ctgtcgtcta cagcacggcc tactacgcgc tggtggtgcg tgggcgggtg cgccccgggg   5160
agacgctgct catccactcg ggctcggcg gcgtgggcca ggccgccatc gccatcgccc    5220
tcagtctggg ctgccgcgtc ttcaccaccg tggggtcggc tgagaagcgg gcgtacctcc   5280
aggccaggtt cccccagctc gacagcacca gcttcgccaa ctcccgggac acatccttcg   5340
agcagcatgt gctgtggcac acgggcggga agggcgttga cctggtcttg aactccttgg   5400
cggaagagaa gctgcaggcc agcgtgaggt gcttggctac gcacggtcgc ttcctggaaa   5460
ttggcaaatt cgacctttct cagaaccacc cgctcggcat ggctatcttc ctgaagaacg   5520
tgacattcca cggggtccta ctggatgcgt tcttcaacga gagcagtgct gactggcggg   5580
aggtgtgggc gcttgtgcag gccggcatcc gggatggggt ggtacggccc ctcaagtgca   5640
cggtgttcca tggggcccag gtggaggacg ccttccgcta catggcccaa gggaagcaca   5700
ttggcaaagt cgtcgtgcag gtgcttgcgg aggagccgga ggcagtgctg aaggggggcca  5760 aacccaagct gatgtcggcc atctccaaga ccttctgccc ggcccacaag agctacatca   5820
tcgctggtgg tctgggtggc ttcggcctgg agttggcgca gtggctgata cagcgtgggg   5880
tgcagaagct cgtgttgact ctcgctccg ggatccggac aggctaccag gccaagcagg    5940
tccgccggtg gaggcgccag ggcgtacagg tgcaggtgtc caccagcaac atcagctcac   6000 tggaggggc ccggggcctc attgccgagg cggcgcagct gggcccgtg ggcggcgtct     6060 tcaacctggc cgtggtcttg agagatggct tgctggagaa ccagacccca gagttcttcc   6120
aggacgtctg caagcccaag tacagcggca ccctgaacct ggacagggtg acccgagagg   6180
cgtgccctga gctggactac tttgtggtct tctcctctgt gagctgcggg cgtggcaatg   6240
cgggacagag caactacggc tttgccaatt ccgccatgga gcgtatctgt gagaaacgcc   6300
ggcacgaagg cctcccaggc ctggccgtgc agtggggcgc catcggcgac gtgggcattt   6360
tggtggagac gatgagcacc aacgacacga tcgtcagtgg cacgctgccc cagcgcatgg   6420
cgtcctgcct ggaggtgctg gacctcttcc tgaaccagcc ccacatggtc ctgagcagct   6480
ttgtgctggc tgagaaggct gcggcctata gggacaggga cagccagcgg gacctggtgg   6540
aggccgtggc acacattctg ggcatccgcg acttggctgc tgtcaacctg gacagctcac   6600
tggcggacct gggcctggac tcgctcatga gcgtggaggt gcgccagacg ctggagcgtg   6660
agctcaacct ggtgctgtcc gtgcgcgagg tgcggcaact cacgctccgg aaactgcagg   6720
agctgtcctc aaaggcggat gaggcagcg agctggcatg cccacgcccc aaggaggatg    6780
gtctggccca gcagcagact cagctgaacc tgcgctccct gctggtgaac ccggagggcc   6840
```

-continued

```
ccaccctgat gcggctcaac tccgtgcaga gctcggagcg gcccctgttc ctggtgcacc      6900
caatcgaggg ctccaccacc gtgttccaca gcctggcctc ccggctcagc atccccacct      6960
atggcctgca gtgcacccga gctgcgcccc ttgacagcat ccacagcctg ctgcctact       7020 acatcgactg catcaggcag gtgcagcccg agggccccta ccgcgtggcc ggctactcct      7080
acggggcctg cgtggccttt gaaatgtgct cccagctgca ggcccagcag agcccagccc      7140
ccacccacaa cagcctcttc ctgttcgacg gctcgcccac ctacgtactg gcctacaccc      7200
agagctaccg ggcaaagctg acccaggct gtgaggctga ggctgagacg gaggccatat       7260
gcttcttcgt gcagcagttc acggacatgg agcacaacag ggtgctggag gcgctgctgc      7320
cgctgaaggg cctagaggag cgtgtggcag ccgccgtgga cctgatcatc aagagccacc      7380
agggcctgga ccgccaggag ctgagctttg cggcccggtc cttctactac aagctgcgtg      7440
ccgctgagca gtacacaccc aaggccaagt accatggcaa cgtgatgcta ctgcgcgcca      7500
agacgggtgg cgcctacggc gaggacctgg gcgcggacta caacctctcc caggtatgcg      7560
acgggaaagt atccgtccac gtcatcgagg gtgaccaccg cacgctgctg gagggcagcg      7620
gcctggagtc catcatcagc atcatccaca gctccctggc tgagccacgc gtgagcgtgc      7680
gggagggcta ggcccgtgcc cccgcctgcc accggaggtc actccaccat ccccacccca      7740
ccccacccca ccccgccat gcaacgggat tgaagggtcc tgccggtggg accctgtccg       7800
gcccagtgcc actgccccccc gaggctgcta gacgtaggtg ttaggcatgt cccacccacc     7860
cgccggcttc cacggcacct ggggacacc agagctgccg acttggagac tcctggtctg      7920
tgaagaccgg tggtgcccgt gcccgcagga actgggctgg gcctcgtgcg cccgtggggt      7980
ctgcgcttgg tctttctgtg cttggatttg catatttatt gcattgctgg tagagacccc      8040
caggcctgtc caccctgcca agactcctca ggcagcgtgt gggtcccgca ctctgccccc      8100
atttccccga tgtcccctgc gggcgcgggc agccacccaa gcctgctggc tgcggccccc      8160
tctcggccag gcattggctc agcccgctga gtgggggtc gtgggccagt ccccgaggag       8220
ctgggcccct gcacaggcac acagggcccg gccacaccca gcggcccccc gcacagccac      8280
ccgtggggtg ctgcccttat gcccggcgcc gggcaccaac tccatgtttg gtgtttgtct      8340
gtgtttgttt ttcaagaaat gattcaaatt gctgcttgga ttttgaaatt tactgtaact      8400
gtcagtgtac acgtctggac cccgtttcat ttttacacca atttggtaaa aatgctgctc      8460
tcagcctccc acaattaaac cgcatgtgat ctccaaaaaa aaaaaaaaag gcggccgc        8519
```

<210> SEQ ID NO 2
<211> LENGTH: 2511
<212> TYPE: PRT
<213> ORGANISM: HOMO SAPIENS

<400> SEQUENCE: 2

```
Met Glu Glu Val Val Ile Ala Gly Met Ser Gly Lys Leu Pro Glu Ser
1               5                   10                  15

Glu Asn Leu Gln Glu Phe Trp Asp Asn Leu Ile Gly Gly Val Asp Met
            20                  25                  30

Val Thr Asp Asp Asp Arg Arg Trp Lys Ala Gly Leu Tyr Gly Leu Pro
        35                  40                  45

Arg Arg Ser Gly Lys Leu Lys Asp Leu Ser Arg Phe Asp Ala Ser Phe
    50                  55                  60

Phe Gly Val His Pro Lys Gln Ala His Thr Met Asp Pro Gln Leu Arg
65                  70                  75                  80
```

-continued

```
Leu Leu Leu Glu Val Thr Tyr Glu Ala Ile Val Asp Gly Gly Ile Asn
                 85                  90                  95
Pro Asp Ser Leu Arg Gly Thr His Thr Gly Val Trp Val Gly Val Ser
            100                 105                 110
Gly Ser Glu Thr Ser Glu Ala Leu Ser Arg Asp Pro Glu Thr Leu Val
        115                 120                 125
Gly Tyr Ser Met Val Gly Cys Gln Arg Ala Met Met Ala Asn Arg Leu
    130                 135                 140
Ser Phe Phe Phe Asp Phe Arg Gly Pro Ser Ile Ala Leu Asp Thr Ala
145                 150                 155                 160
Cys Ser Ser Ser Leu Met Ala Leu Gln Asn Ala Tyr Gln Ala Ile His
                165                 170                 175
Ser Gly Gln Cys Pro Ala Ala Ile Val Gly Gly Ile Asn Val Leu Leu
            180                 185                 190
Lys Pro Asn Thr Ser Val Gln Phe Leu Arg Leu Gly Met Leu Ser Pro
        195                 200                 205
Glu Gly Thr Cys Lys Ala Phe Asp Thr Ala Gly Asn Gly Tyr Cys Arg
    210                 215                 220
Ser Glu Gly Val Val Ala Val Leu Leu Thr Lys Lys Ser Leu Ala Arg
225                 230                 235                 240
Arg Val Tyr Ala Thr Ile Leu Asn Ala Gly Thr Asn Thr Asp Gly Phe
                245                 250                 255
Lys Glu Gln Gly Val Thr Phe Pro Ser Gly Asp Ile Gln Glu Gln Leu
            260                 265                 270
Ile Arg Ser Leu Tyr Gln Ser Ala Gly Val Ala Pro Glu Ser Phe Glu
        275                 280                 285
Tyr Ile Glu Ala His Gly Thr Gly Thr Lys Val Gly Asp Pro Gln Glu
    290                 295                 300
Leu Asn Gly Ile Thr Arg Ala Leu Cys Ala Thr Arg Gln Glu Pro Leu
305                 310                 315                 320
Leu Ile Gly Ser Thr Lys Ser Asn Met Gly His Pro Glu Pro Ala Ser
                325                 330                 335
Gly Leu Ala Ala Leu Ala Lys Val Leu Leu Ser Leu Glu His Gly Leu
            340                 345                 350
Trp Ala Pro Asn Leu His Phe His Ser Pro Asn Pro Glu Ile Pro Ala
        355                 360                 365
Leu Leu Asp Gly Arg Leu Gln Val Val Asp Gln Pro Leu Pro Val Arg
    370                 375                 380
Gly Gly Asn Val Gly Ile Asn Ser Phe Gly Phe Gly Gly Ser Asn Val
385                 390                 395                 400
His Ile Ile Leu Arg Pro Asn Thr Gln Pro Pro Ala Pro Ala Pro
                405                 410                 415
His Ala Thr Leu Pro Arg Leu Leu Arg Ala Ser Gly Arg Thr Pro Glu
            420                 425                 430
Ala Val Gln Lys Leu Leu Glu Gln Gly Leu Arg His Ser Gln Asp Leu
        435                 440                 445
Ala Phe Leu Ser Met Leu Asn Asp Ile Ala Ala Val Pro Ala Thr Ala
    450                 455                 460
Met Pro Phe Arg Gly Tyr Ala Val Leu Gly Gly Glu Arg Gly Gly Pro
465                 470                 475                 480
Glu Val Gln Gln Val Pro Ala Gly Glu Arg Pro Leu Trp Phe Ile Cys
                485                 490                 495
```

-continued

```
Ser Gly Met Gly Thr Gln Trp Arg Gly Met Gly Leu Ser Leu Met Arg
            500                 505                 510

Leu Asp Arg Phe Arg Asp Ser Ile Leu Arg Ser Asp Glu Ala Val Lys
            515                 520                 525

Pro Phe Gly Leu Lys Val Ser Gln Leu Leu Ser Thr Asp Glu Ser
            530                 535                 540

Thr Phe Asp Asp Ile Val His Ser Phe Val Ser Leu Thr Ala Ile Gln
545                 550                 555                 560

Ile Gly Leu Ile Asp Leu Leu Ser Cys Met Gly Leu Arg Pro Asp Gly
                565                 570                 575

Ile Val Gly His Ser Leu Gly Glu Val Ala Cys Gly Tyr Ala Asp Gly
            580                 585                 590

Cys Leu Ser Gln Glu Glu Ala Val Leu Ala Ala Tyr Trp Arg Gly Gln
            595                 600                 605

Cys Ile Lys Glu Ala His Leu Pro Pro Gly Ala Met Ala Ala Val Gly
            610                 615                 620

Leu Ser Trp Glu Glu Cys Lys Gln Arg Cys Pro Pro Gly Val Val Pro
625                 630                 635                 640

Ala Cys His Asn Ser Lys Asp Thr Val Thr Ile Ser Gly Pro Gln Ala
                645                 650                 655

Pro Val Phe Glu Phe Val Glu Gln Leu Arg Lys Glu Gly Val Phe Ala
            660                 665                 670

Lys Glu Val Arg Thr Gly Gly Met Ala Phe His Ser Tyr Phe Met Glu
            675                 680                 685

Ala Ile Ala Pro Pro Leu Leu Gln Glu Leu Lys Lys Val Ile Arg Glu
            690                 695                 700

Pro Lys Pro Arg Ser Ala Arg Trp Leu Ser Thr Ser Ile Pro Glu Ala
705                 710                 715                 720

Gln Trp His Ser Ser Leu Ala Arg Thr Ser Ser Ala Glu Tyr Asn Val
                725                 730                 735

Asn Asn Leu Val Ser Pro Val Leu Phe Gln Glu Ala Leu Trp His Val
                740                 745                 750

Pro Glu His Ala Val Val Leu Glu Ile Ala Pro His Ala Leu Leu Gln
            755                 760                 765

Ala Val Leu Lys Arg Gly Leu Lys Pro Ser Cys Thr Ile Ile Pro Leu
            770                 775                 780

Met Lys Lys Asp His Arg Asp Asn Leu Glu Phe Phe Leu Ala Gly Ile
785                 790                 795                 800

Gly Arg Leu His Leu Ser Gly Ile Asp Ala Asn Pro Asn Ala Leu Phe
                805                 810                 815

Pro Pro Val Glu Phe Pro Ala Pro Arg Gly Thr Pro Leu Ile Ser Pro
            820                 825                 830

Leu Ile Lys Trp Asp His Ser Leu Ala Trp Asp Val Pro Ala Ala Glu
            835                 840                 845

Asp Phe Pro Asn Gly Ser Gly Ser Pro Ser Ala Ala Ile Tyr Asn Ile
            850                 855                 860

Asp Thr Ser Ser Glu Ser Pro Asp His Tyr Leu Val Asp His Thr Leu
865                 870                 875                 880

Asp Gly Arg Val Leu Phe Pro Ala Thr Gly Tyr Leu Ser Ile Val Trp
                885                 890                 895

Lys Thr Leu Ala Arg Ala Leu Gly Leu Gly Val Glu Gln Leu Pro Val
            900                 905                 910
```

```
Val Phe Glu Asp Val Val Leu His Gln Ala Thr Ile Leu Pro Lys Thr
        915                 920                 925

Gly Thr Val Ser Leu Glu Val Arg Leu Leu Glu Ala Ser Arg Ala Phe
        930                 935                 940

Glu Val Ser Glu Asn Gly Asn Leu Val Val Ser Gly Lys Val Tyr Gln
945                 950                 955                 960

Trp Asp Asp Pro Asp Pro Arg Leu Phe Asp His Pro Glu Ser Pro Thr
                965                 970                 975

Pro Asn Pro Thr Glu Pro Leu Phe Leu Ala Gln Ala Glu Val Tyr Lys
            980                 985                 990

Glu Leu Arg Leu Arg Gly Tyr Asp Tyr Gly Pro His Phe Gln Gly Ile
        995                 1000                1005

Leu Glu Ala Ser Leu Glu Gly Asp Ser Gly Arg Leu Leu Trp Lys Asp
        1010                1015                1020

Asn Trp Val Ser Phe Met Asp Thr Met Leu Gln Met Ser Ile Leu Gly
1025                1030                1035                1040

Ser Ala Lys His Gly Leu Tyr Leu Pro Thr Arg Val Thr Ala Ile His
            1045                1050                1055

Ile Asp Pro Ala Thr His Arg Gln Lys Leu Tyr Thr Leu Gln Asp Lys
            1060                1065                1070

Ala Gln Val Ala Asp Val Val Ser Arg Trp Leu Arg Val Thr Val
        1075                1080                1085

Ala Gly Gly Val His Ile Ser Gly Leu His Thr Glu Ser Ala Pro Arg
        1090                1095                1100

Arg Gln Gln Glu Gln Gln Val Pro Ile Leu Glu Lys Phe Cys Phe Thr
1105                1110                1115                1120

Pro His Thr Glu Glu Gly Cys Leu Ser Glu Arg Ala Ala Leu Gln Glu
            1125                1130                1135

Glu Leu Gln Leu Cys Lys Gly Leu Val Gln Ala Leu Gln Thr Lys Val
            1140                1145                1150

Thr Gln Gln Gly Leu Lys Met Val Val Pro Gly Leu Asp Gly Ala Gln
            1155                1160                1165

Ile Pro Arg Asp Pro Ser Gln Gln Glu Leu Pro Arg Leu Leu Ser Ala
        1170                1175                1180

Ala Cys Arg Leu Gln Leu Asn Gly Asn Leu Gln Leu Glu Leu Ala Gln
1185                1190                1195                1200

Val Leu Ala Gln Glu Arg Pro Lys Leu Pro Glu Asp Pro Leu Leu Ser
            1205                1210                1215

Gly Leu Leu Asp Ser Pro Ala Leu Lys Ala Cys Leu Asp Thr Ala Val
            1220                1225                1230

Glu Asn Met Pro Ser Leu Lys Met Lys Val Val Glu Val Leu Ala Gly
            1235                1240                1245

His Gly His Leu Tyr Ser Arg Ile Pro Gly Leu Leu Ser Pro His Pro
            1250                1255                1260

Leu Leu Gln Leu Ser Tyr Thr Ala Thr Asp Arg His Pro Gln Ala Leu
1265                1270                1275                1280

Glu Ala Ala Gln Ala Glu Leu Gln Gln His Asp Val Ala Gln Gly Gln
            1285                1290                1295

Trp Asp Pro Ala Asp Pro Ala Pro Ser Ala Leu Gly Ser Ala Asp Leu
            1300                1305                1310

Leu Val Cys Asn Cys Ala Val Ala Ala Leu Gly Asp Pro Ala Ser Ala
            1315                1320                1325
```

-continued

```
Leu Ser Asn Met Val Ala Ala Leu Arg Glu Gly Gly Phe Leu Leu Leu
            1330            1335                1340

His Thr Leu Leu Arg Gly His Pro Leu Gly Asp Ile Val Ala Phe Leu
1345                1350                1355                1360

Thr Ser Thr Glu Pro Gln Tyr Gly Gln Gly Ile Leu Ser Gln Asp Ala
                1365                1370                1375

Trp Glu Ser Leu Phe Ser Arg Val Ser Leu Arg Leu Val Gly Leu Lys
            1380                1385                1390

Lys Ser Phe Tyr Gly Ser Thr Leu Phe Leu Cys Arg Arg Pro Thr Pro
            1395                1400                1405

Gln Asp Ser Pro Ile Phe Leu Pro Val Asp Asp Thr Ser Phe Arg Trp
1410                1415                1420

Val Glu Ser Leu Lys Gly Ile Leu Ala Asp Glu Asp Ser Ser Arg Pro
1425                1430                1435                1440

Val Trp Leu Lys Ala Ile Asn Cys Ala Thr Ser Gly Val Val Gly Leu
                1445                1450                1455

Val Asn Cys Leu Arg Arg Glu Pro Gly Gly Asn Arg Leu Arg Cys Val
            1460                1465                1470

Leu Leu Ser Asn Leu Ser Ser Thr Ser His Val Pro Glu Val Asp Pro
            1475                1480                1485

Gly Ser Ala Glu Leu Gln Lys Val Leu Gln Gly Asp Leu Val Met Asn
            1490                1495                1500

Val Tyr Arg Asp Gly Ala Trp Gly Ala Phe Arg His Phe Leu Leu Glu
1505                1510                1515                1520

Glu Asp Lys Pro Glu Glu Pro Thr Ala His Ala Phe Val Ser Thr Leu
                1525                1530                1535

Thr Arg Gly Asp Leu Ser Ser Ile Arg Trp Val Cys Ser Ser Leu Arg
            1540                1545                1550

His Ala Gln Pro Thr Cys Pro Gly Ala Gln Leu Cys Thr Val Tyr Tyr
            1555                1560                1565

Ala Ser Leu Asn Phe Arg Asp Ile Met Leu Ala Thr Gly Lys Leu Ser
            1570                1575                1580

Pro Asp Ala Ile Pro Gly Lys Trp Thr Ser Gln Asp Ser Leu Leu Gly
1585                1590                1595                1600

Met Glu Phe Ser Gly Arg Asp Ala Ser Gly Lys Arg Val Met Gly Leu
                1605                1610                1615

Val Pro Ala Lys Gly Leu Ala Thr Ser Val Leu Leu Ser Pro Asp Phe
            1620                1625                1630

Leu Trp Asp Val Pro Ser Asn Trp Thr Leu Glu Glu Ala Ala Ser Val
            1635                1640                1645

Pro Val Val Tyr Ser Thr Ala Tyr Tyr Ala Leu Val Val Arg Gly Arg
            1650                1655                1660

Val Arg Pro Gly Glu Thr Leu Leu Ile His Ser Gly Ser Gly Gly Val
1665                1670                1675                1680

Gly Gln Ala Ala Ile Ala Ile Ala Leu Ser Leu Gly Cys Arg Val Phe
                1685                1690                1695

Thr Thr Val Gly Ser Ala Glu Lys Arg Ala Tyr Leu Gln Ala Arg Phe
            1700                1705                1710

Pro Gln Leu Asp Ser Thr Ser Phe Ala Asn Ser Arg Asp Thr Ser Phe
            1715                1720                1725

Glu Gln His Val Leu Trp His Thr Gly Gly Lys Gly Val Asp Leu Val
            1730                1735                1740
```

-continued

```
Leu Asn Ser Leu Ala Glu Glu Lys Leu Gln Ala Ser Val Arg Cys Leu
1745                1750                1755                1760

Ala Thr His Gly Arg Phe Leu Glu Ile Gly Lys Phe Asp Leu Ser Gln
            1765                1770                1775

Asn His Pro Leu Gly Met Ala Ile Phe Leu Lys Asn Val Thr Phe His
            1780                1785                1790

Gly Val Leu Leu Asp Ala Phe Phe Asn Glu Ser Ser Ala Asp Trp Arg
            1795                1800                1805

Glu Val Trp Ala Leu Val Gln Ala Gly Ile Arg Asp Gly Val Val Arg
    1810                1815                1820

Pro Leu Lys Cys Thr Val Phe His Gly Ala Gln Val Glu Asp Ala Phe
1825                1830                1835                1840

Arg Tyr Met Ala Gln Gly Lys His Ile Gly Lys Val Val Gln Val
            1845                1850                1855

Leu Ala Glu Glu Pro Glu Ala Val Leu Lys Gly Ala Lys Pro Lys Leu
            1860                1865                1870

Met Ser Ala Ile Ser Lys Thr Phe Cys Pro Ala His Lys Ser Tyr Ile
            1875                1880                1885

Ile Ala Gly Gly Leu Gly Gly Phe Gly Leu Glu Leu Ala Gln Trp Leu
    1890                1895                1900

Ile Gln Arg Gly Val Gln Lys Leu Val Leu Thr Ser Arg Ser Gly Ile
1905                1910                1915                1920

Arg Thr Gly Tyr Gln Ala Lys Gln Val Arg Arg Trp Arg Arg Gln Gly
            1925                1930                1935

Val Gln Val Gln Val Ser Thr Ser Asn Ile Ser Ser Leu Glu Gly Ala
            1940                1945                1950

Arg Gly Leu Ile Ala Glu Ala Ala Gln Leu Gly Pro Val Gly Gly Val
            1955                1960                1965

Phe Asn Leu Ala Val Val Leu Arg Asp Gly Leu Leu Glu Asn Gln Thr
    1970                1975                1980

Pro Glu Phe Phe Gln Asp Val Cys Lys Pro Lys Tyr Ser Gly Thr Leu
1985                1990                1995                2000

Asn Leu Asp Arg Val Thr Arg Glu Ala Cys Pro Glu Leu Asp Tyr Phe
            2005                2010                2015

Val Val Phe Ser Ser Val Ser Cys Gly Arg Gly Asn Ala Gly Gln Ser
            2020                2025                2030

Asn Tyr Gly Phe Ala Asn Ser Ala Met Glu Arg Ile Cys Glu Lys Arg
            2035                2040                2045

Arg His Glu Gly Leu Pro Gly Leu Ala Val Gln Trp Gly Ala Ile Gly
            2050                2055                2060

Asp Val Gly Ile Leu Val Glu Thr Met Ser Thr Asn Asp Thr Ile Val
2065                2070                2075                2080

Ser Gly Thr Leu Pro Gln Arg Met Ala Ser Cys Leu Glu Val Leu Asp
            2085                2090                2095

Leu Phe Leu Asn Gln Pro His Met Val Leu Ser Ser Phe Val Leu Ala
            2100                2105                2110

Glu Lys Ala Ala Ala Tyr Arg Asp Arg Asp Ser Gln Arg Asp Leu Val
            2115                2120                2125

Glu Ala Val Ala His Ile Leu Gly Ile Arg Asp Leu Ala Ala Val Asn
            2130                2135                2140

Leu Asp Ser Ser Leu Ala Asp Leu Gly Leu Asp Ser Leu Met Ser Val
2145                2150                2155                2160
```

-continued

```
Glu Val Arg Gln Thr Leu Glu Arg Glu Leu Asn Leu Val Leu Ser Val
                2165                2170                2175

Arg Glu Val Arg Gln Leu Thr Leu Arg Lys Leu Gln Glu Leu Ser Ser
            2180                2185                2190

Lys Ala Asp Glu Ala Ser Glu Leu Ala Cys Pro Thr Pro Lys Glu Asp
        2195                2200                2205

Gly Leu Ala Gln Gln Gln Thr Gln Leu Asn Leu Arg Ser Leu Leu Val
    2210                2215                2220

Asn Pro Glu Gly Pro Thr Leu Met Arg Leu Asn Ser Val Gln Ser Ser
2225                2230                2235                2240

Glu Arg Pro Leu Phe Leu Val His Pro Ile Glu Gly Ser Thr Thr Val
                2245                2250                2255

Phe His Ser Leu Ala Ser Arg Leu Ser Ile Pro Thr Tyr Gly Leu Gln
                2260                2265                2270

Cys Thr Arg Ala Ala Pro Leu Asp Ser Ile His Ser Leu Ala Ala Tyr
            2275                2280                2285

Tyr Ile Asp Cys Ile Arg Gln Val Gln Pro Glu Gly Pro Tyr Arg Val
        2290                2295                2300

Ala Gly Tyr Ser Tyr Gly Ala Cys Val Ala Phe Glu Met Cys Ser Gln
2305                2310                2315                2320

Leu Gln Ala Gln Gln Ser Pro Ala Pro Thr His Asn Ser Leu Phe Leu
                2325                2330                2335

Phe Asp Gly Ser Pro Thr Tyr Val Leu Ala Tyr Thr Gln Ser Tyr Arg
            2340                2345                2350

Ala Lys Leu Thr Pro Gly Cys Glu Ala Glu Ala Glu Thr Glu Ala Ile
            2355                2360                2365

Cys Phe Phe Val Gln Gln Phe Thr Asp Met Glu His Asn Arg Val Leu
        2370                2375                2380

Glu Ala Leu Leu Pro Leu Lys Gly Leu Glu Glu Arg Val Ala Ala Ala
2385                2390                2395                2400

Val Asp Leu Ile Ile Lys Ser His Gln Gly Leu Asp Arg Gln Glu Leu
                2405                2410                2415

Ser Phe Ala Ala Arg Ser Phe Tyr Tyr Lys Leu Arg Ala Ala Glu Gln
            2420                2425                2430

Tyr Thr Pro Lys Ala Lys Tyr His Gly Asn Val Met Leu Leu Arg Ala
            2435                2440                2445

Lys Thr Gly Gly Ala Tyr Gly Glu Asp Leu Gly Ala Asp Tyr Asn Leu
        2450                2455                2460

Ser Gln Val Cys Asp Gly Lys Val Ser Val His Val Ile Glu Gly Asp
2465                2470                2475                2480

His Arg Thr Leu Leu Glu Gly Ser Gly Leu Glu Ser Ile Ile Ser Ile
                2485                2490                2495

Ile His Ser Ser Leu Ala Glu Pro Arg Val Ser Val Arg Glu Gly
            2500                2505                2510
```

HUMAN FAS

FIELD OF THE INVENTION

This invention relates to newly identified polypeptides and polynucleotides encoding such polypeptides, to their use in therapy and in identifying compounds which may be agonists, antagonists and/or inhibitors which are potentially useful in therapy, and to production of such polypeptides and polynucleotides.

BACKGROUND OF THE INVENTION

The drug discovery process is currently undergoing a fundamental revolution as it embraces 'functional genomics', that is, high throughput genome- or gene-based biology. This approach is rapidly superseding earlier approaches based on 'positional cloning'. A phenotype, that is a biological function or genetic disease, would be identified and this would then be tracked back to the responsible gene, based on its genetic map position.

Functional genomics relies heavily on the various tools of bioinformatics to identify gene sequences of potential interest from the many molecular biology databases now available. There is a continuing need to identify and characterise further genes and their related polypeptides/proteins, as targets for drug discovery.

While the pathway for the biosynthesis of saturated fatty acids is similar in prokaryotes and eukaryotes, the organization of the biosynthetic apparatus is very different. Vertebrates and yeast possess fatty acid synthases (FASs) in which all of the enzymatic activities are encoded on one or two polypeptide chains, respectively, and the acyl carrier protein (ACP) is an integral part of the complex. In contrast, in most bacterial FASs each of the reactions are catalyzed by distinct monofunctional enzymes and the ACP is a discrete protein. There therefore is considerable potential for selective inhibition of the bacterial systems by broad spectrum antibacterial agents.

SUMMARY OF THE INVENTION

The present invention relates to Fatty Acid Synthase, in particular Fatty Acid Synthase polypeptides and Fatty Acid Synthase polynucleotides, recombinant materials and methods for their production. In another aspect, the invention relates to methods for using such polypeptides and polynucleotides, including the treatment of cancers and bacterial infections, hereinafter referred to as "the Diseases", amongst others. In a further aspect, the invention relates to methods for identifying agonists and antagonists/inhibitors using the materials provided by the invention, and treating conditions associated with Fatty Acid Synthase imbalance with the identified compounds. In a still further aspect, the invention relates to diagnostic assays for detecting diseases associated with inappropriate Fatty Acid Synthase activity or levels.

DESCRIPTION OF THE INVENTION

In a first aspect, the present invention relates to Fatty Acid Synthase polypeptides. Such peptides include isolated polypeptides comprising an amino acid sequence which has at least 70% identity, preferably at least 80% identity, more preferably at least 90% identity, yet more preferably at least 95% identity, Ynost preferably at least 97–99% identity, to that of SEQ ID NO:2 over the entire length of SEQ ID NO:2. Such polypeptides include those comprising the amino acid of SEQ ID NO:2.

Further peptides of the present invention include isolated polypeptides in which the amino acid sequence has at least 70% identity, preferably at least 80% identity, more preferably at least 90% identity, yet more preferably at least 95% identity, most preferably at least 97–99% identity, to the amino acid sequence of SEQ ID NO:2 over the entire length of SEQ ID NO:2. Such polypeptides include the polypeptide of SEQ ID NO:2.

Further peptides of the present invention include isolated polypeptides encoded by a polynucleotide comprising the sequence contained in SEQ ID NO:1.

Polypeptides of the present invention are believed to be members of the Fatty Acid Synthase family of polypeptides. They are therefore of interest because inhibitors of FAS1 may function as cytotoxic agents with potential as anti-cancer agents and the polypeptides of the present invention provide a tool in the development of potential novel anti-bacterials. These properties are hereinafter referred to as "Fatty Acid Synthase activity" or "Fatty Acid Synthase polypeptide activity" or "biological activity of Fatty Acid Synthase." Also included amongst these activities are antigenic and immunogenic activities of said Fatty Acid Synthase polypeptides, in particular the antigenic and immunogenic activities of the polypeptide of SEQ ID NO:2. Preferably, a polypeptide of the present invention exhibits at least one biological activity of Fatty Acid Synthase.

The polypeptides of the present invention may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

The present invention also includes include variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to Fatty Acid Synthase polynucleotides. Such polynucleotides include isolated polynucleotides comprising a nucleotide sequence encoding a polypeptide which has at least 70% identity, preferably at least 80% identity, more preferably at least 90% identity, yet more preferably at least 95% identity, to the amino acid sequence of SEQ ID NO:2, over the entire length of SEQ ID NO:2. In this regard, polypeptides which have at least 97% identity are highly preferred, whilst those with at least 98–99% identity are more highly preferred, and those with at least 99% identity are most highly preferred. Such polynucleotides include a polynucleotide comprising the nucleotide sequence contained in SEQ ID NO:1 encoding the polypeptide of SEQ ID NO:2.

Further polynucleotides of the present invention include isolated polynucleotides comprising a nucleotide sequence that has at least 70% identity, preferably at least 80% identity, more preferably at least 90% identity, yet more preferably at least 95% identity, to a nucleotide sequence encoding a polypeptide of SEQ ID NO:2, over the entire coding region. In this regard, polynucleotides which have at least 97% identity are highly preferred, whilst those with at least 98–99% identity are more highly preferred, and those with at least 99% identity are most highly preferred.

Further polynucleotides of the present invention include isolated polynucleotides comprising a nucleotide sequence which has at least 70% identity, preferably at least 80% identity, more preferably at least 90% identity, yet more preferably at least 95% identity, to SEQ ID NO:1 over the entire length of SEQ ID NO:1. In this regard, polynucleotides which have at least 97% identity are highly preferred, whilst those with at least 98–99% identify are more highly preferred, and those with at least 99% identity are most highly preferred. Such polynucleotides include a polynucleotide comprising the polynucleotide of SEQ ID NO:1 as well as the polynucleotide of SEQ ID NO:1.

The invention also provides polynucleotides which are complementary to all the above described polynucleotides.

The nucleotide sequence of SEQ ID NO:1 shows homology with Tumor-associated FAS (GenBank accession number: U29344). The nucleotide sequence of SEQ ID NO:1 is a cDNA sequence and comprises a polypeptide encoding sequence (nucleotide 156 to 7688) encoding a polypeptide of 2511 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2. The polypeptide of SEQ ID NO:2 is structurally related to other proteins of the Fatty Acid Synthase family, having homology and/or structual similarity with Tumor-associated FAS (GenBank accession number: U29344).

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one Fatty Acid Synthase activity.

Polynucleotides of the present invention may be obtained, using standard cloning and screening techniques, from a cDNA library derived from mRNA in cells of human testis, using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in SEQ ID NO:1, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding homologs and orthologs from species other than human) that have a high sequence similarity to SEQ ID NO:1. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides.

A polynucleotide encoding a polypeptide of the present invention, including homologs and orthologs from species other than human, may be obtained by a process which comprises the steps of screening an appropriate library under stringent hybridization conditions with a labeled probe having the sequence of SEQ ID NO:1 or a fragment thereof, and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 microgram/ml denatured, sheared salmon sperm DNA; followed by washing the filters in 0.1×SSC at about 65° C. Thus the present invention also includes polynucleotides obtainable by screening an appropriate library under stringent hybridization conditions with a labeled probe having the sequence of SEQ ID NO:1 or a fragment thereof.

The skilled artisan will appreciate that, in many cases, an isolated cDNA sequence will be incomplete, in that the region coding for the polypeptide is cut short at the 5' end of the cDNA. This is a consequence of reverse transcriptase, an enzyme with inherently low 'processivity' (a measure of the ability of the enzyme to remain attached to the template during the polymerisation reaction), failing to complete a DNA copy of the mRNA template during 1st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998–9002, 1988). Recent modifications of the technique, exemplified by the MarathonTm technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression system. Accordingly, in a further aspect, the present invention relates to expression systems which comprise a polynucleotide or polynucleotides of the present invention, to host cell which are genetically engineered with such expression system and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression system or portions thereof for polynucleotides of the present invention. Introduction of polynucleotides into host cells can be effected by methods described in many standard laboratory manuals, such as Davis et al., Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression system can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

This invention also relates to the use of polynucleotides of the present invention as diagnostic reagents. Detection of a mutated form of the gene characteried by the polynucleotide of SEQ ID NO:1 which is associated with a dysfunction will provide a diagnostic tool that can add to, or define, a diagnosis of a disease, or susceptibility to a disease, which results from under-expression, over-expression or altered expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled Fatty Acid Synthase nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (e.g., Myers et al., *Science* (1985)230:1242). Sequence changes at specific locations may also be revealed by nuclease protection assays, such as RNase and S1 protection or the chemical cleavage method (see Cotton et al., *Proc Natl Acad Sci USA* (1985) 85: 4397–4401). In another embodiment, an array of oligonucleotides probes comprising Fatty Acid Synthase nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol 274, pp 610–613 (1996)).

The diagnostic assays offer a process for diagnosing or determining a susceptibility to the Diseases through detection of mutation in the Fatty Acid Synthase gene by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit which comprises:

(a) a polynucleotide of the present invention, preferably the nucleotide sequence of SEQ ID NO:1, or a fragment thereof;

(b) a nucleotide sequence complementary to that of (a);

(c) a polypeptide of the present invention, preferably the polypeptide of SEQ ID NO:2 or a fragment thereof; or (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, particularly cancers and the treatment of bacterial infections, amongst others.

The nucleotide sequences of the present invention are also valuable for chromosome identification. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495497), the trioma technique, the human B-cell hybridoma technique (Kozbor et al., *Immunology Today* (1983) 4:72) and the EBV-hybridoma technique (Cole et al., *MONOCLONAL ANTIBODIES AND CANCER THERAPY*, pp. 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

Antibodies against polypeptides of the present invention may also be employed to treat the Diseases, amongst others.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Another aspect of the invention relates to a method for inducing an immunological response in a mammal which comprises inoculating the mammal with a polypeptide of the present invention, adequate to produce antibody and/or T cell immune response to protect said animal from the Diseases hereinbefore mentioned, amongst others. Yet another aspect of the invention relates to a method of inducing immunological response in a mammal which comprises, delivering a polypeptide of the present invention via a vector directing expression of the polynucleotide and coding for the polypeptide in vivo in order to induce such an immunological response to produce antibody to protect said animal from diseases.

A further aspect of the invention relates to an immunological/vaccine formulation (composition) which, when introduced into a mammalian host, induces an immunological response in that mammal to a polypeptide of the present invention wherein the composition comprises a polypeptide or polynucleotide of the present invention. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unitdose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention are responsible for many biological functions, including many disease states, in particular the Diseases hereinbefore mentioned. It is therefore desirous to devise screening methods to identify compounds which stimulate or which inhibit the function of the polypeptide. Accordingly, in a further aspect, the present invention provides for a method of screening compounds to identify those which stimulate or which inhibit the function of the polypeptide. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof (see Coligan et al., *Current Protocols in Immunology* 1(2) :Chapter 5 (1991)).

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring Fatty Acid Synthase activity in the mixture, and comparing the Fatty Acid Synthase activity of the mixture to a standard. Fusion proteins, such as those made from Fc portion and Fatty Acid Synthase polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16) :9459–9471 (1995)).

FAS1 Selectivity Assays

Two approaches have been taken in order to identify compounds selective for bacterial vs. eukaryotic fatty acid synthases, in the absence of the human FAS1 enzyme. One utilized a cleared lysate from *Saccharomyces cerevisiae*, the other a purified enzyme from chicken liver. Human FAS1 will become the selectivity assay of choice as soon as material is available and validated.

*Saccharomyces Cerevisiae* FAS1

Yeast cells were disrupted using glass beads and cell wall debris removed by centrifugation. FAS1 activity was assayed in the presence of acetyl-CoA, NADPH, [$^{14}$C] malonyl-CoA, DTT, and phosphate buffer. TCA precipitation and filtration was used to separate radiolabeled product from substrate.

The High Throughput Assay Conditions are:
25 ul reaction volume, total counts ~2000 CPM, background ~100 CPM
50 mM K3PO4 buffer pH 6.5
45 uM acetyl-CoA
150 uM NADPH
1 mM DTT
90 uM malonyl CoA (mixture of hot and cold) 44K DPM per rxn
10 ug/ml FAS I
37 C for 30 min
precipitate product using TCA, filter, dry and count.
To confirm label was incorporated into fatty acids use the extraction assay (250–500 ul volumes, same concentrations as above) then:
add 0.1 ml of 0.5N NaOH, 100C for 15 minutes
add 0.1 ml of 1N HCl, followed by 2 ml DI water
extract 2 times in 3 ml n-hexane and combine
evaporate under nitrogen add cocktail and count or make the methyl esters by transesterification
using boron triflouride in 14% methanol and separate by TLC
image by phosphor screen or autoradiography Chicken FAS1

Purification included liver homogenization, ammonium sulfate fractionation, gel filtration (Sephacryl S-300) and ion exchange (Q-Sepharose) chromatographies. The enzyme preparation obtained is approximately 90% pure by SDS-PAGE. Activity was measured in the manner outlined for the yeast assay. The activity of this enzyme was shown to be dependent on NADPH and extractable in petroleum ether, consistent with palmitate being the primary reaction product.

Human FAS1

Activity is measured in the manner outlined for the yeast assay.

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The polypeptide may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide which compete with the binding of the polypeptide to its receptors, if any. Standard methods for conducting such assays are well understood in the art.

Examples of potential polypeptide antagonists include antibodies or, in some cases, oligonucleotides or proteins which are closely related to the ligands, substrates, receptors, enzymes, etc., as the case may be, of the polypeptide, e.g., a fiagment of the ligands, substrates, receptors, enzymes, etc.; or small molecules which bind to the polypeptide of the present invention but do not elicit a response, so that the activity of the polypeptide is prevented.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:

(a) a polypeptide of the present invention;

(b) a recombinant cell expressing a polypeptide of the present invention;

(c) a cell membrane expressing a polypeptide of the present invention; or (d) antibody to a polypeptide of the present invention;

which polypeptide is preferably that of SEQ ID NO:2.

It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:

(a) determining in the first instance the three-dimensional structure of the polypeptide;

(b) deducing the three-dimensional structure for the likely reactive or binding site(s) of an agonist, antagonist or inhibitor;

(c) synthesizing candidate compounds that are predicted to bind to or react with the deduced binding or reactive site; and (d) testing whether the candidate compounds are indeed agonists, antagonists or inhibitors.

It will be further appreciated that this will normally be an interactive process.

In a further aspect, the present invention provides methods of treating abnormal conditions such as, for instance, cancers and bacterial infections, related to either an excess of, or an under-expression of, Fatty Acid Synthase polypeptide activity.

If the activity of the polypeptide is in excess, several approaches are available. One approach comprises administering to a subject in need thereof an inhibitor compound (antagonist) as hereinabove described, optionally in combination with a pharmaceutically acceptable carrier, in an amount effective to inhibit the function of the polypeptide, such as, for example, by blocking the binding of ligands, substrates, receptors, enzymes, etc., or by inhibiting a second signal, andthereby alleviating the abnormal condition. In another approach, soluble forms of the polypeptides still capable of binding the ligand, substrate, enzymes, receptors, etc. in competition with endogenous polypeptide may be administered. Typical examples of such competitors include fragments of the Fatty Acid Synthase polypeptide.

In still another approach, expression of the gene encoding endogenous Fatty Acid Synthase polypeptide can be inhibited using expression blocking techniques. Known such techniques involve the use of antisense sequences, either internally generated or separately administered (see, for example, O'Connor, *J Neurochem* (1991) 56:560 in Oligodeoxynucleotides as Antisense Inhibitors of Gene Expression, CRC Press, Boca Raton, FL (1988)). Alternatively, oligonucleotides which form triple helices with the gene can be supplied (see, for example, Lee et al, *Nucleic Acids Res* (1979) 6:3073; Cooney et al., *Science* (1988) 241:456; Dervan et al., *Science* (1991) 251:1360). These oligomers can be administered per se or the relevant oligomers can be expressed in vivo.

For treating abnormal conditions related to an under-expression of Fatty Acid Synthase and its activity, several approaches are also available. One approach comprises admiering to a subject a therapeutically effective amount of a compound which activates apolypeptide of the present invention, i.e., an agonist as described above, in combination with a pharmaceutically acceptable carrier, to thereby alleviate the abnormal condition. Alternatively, gene therapy may be employed to effect the endogenous production of Fatty Acid Synthase by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer a therapeutic amount of a polypeptide of the present invention in combination with a suitable pharmaceutical carrier.

In a further aspect, the present invention provides for pharmaceutical compositions comprising a therapeutically effective amount of a polypeptide, such as the soluble form of a polypeptide of the present invention, agonist/antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Polynucleotide and polypeptide sequences form a valuable information resource with which to identify further sequences of similar homology. This is most easily facilitated by storing the sequence in a computer readable medium and then using the stored data to search a sequence database using well known searching tools, such as GCC. Accordingly, in a further aspect, the present invention provides for a computer readable medium having stored thereon a polynucleotide comprising the sequence of SEQ ID NO:1 and/or a polypeptide sequence encoded thereby.

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, *PROTEINS— STRUCTURE AND MOLECULAR PROPERTIES*, 2nd Ed., T. E. Creighton, W. H. Freeman and Company, New York, 1993; Wold, F., Post-translational Protein Modifications: Perspectives and Prospects, pgs. 1–12 in *POSTTRANSLATIONAL COVALENT MODIFICATION OF PROTEINS*, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Post-translational Modifications and Aging", *Ann NY Acad Sci* (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, MD 20894; Altschul, S., et al., *J. Mol. Biol.* 215: 403–410 (1990). The well known SmithWaterman algorithm may also be used to determine identity.

Preferred parameters for polypeptide sequence comparison include the following:

1) Algorithm: Needleman and Wunsch, J. Mol Biol. 48: 443–453 (1970)
   Comparison matrix: BLOSSUM62 from Hentikoff and Hentikoff, Proc. Natl. Acad. Sci. USA. 89:10915–10919 (1992)
   Gap Penalty: 12
   Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:

1) Algorithm: Needleman and Wunsch, J. Mol Biol. 48: 443–453 (1970)
   Comparison matrix: matches=+10, mismatch=0
   Gap Penalty: 50
   Gap Length Penalty: 3
   Available as: The "gap" program from Genetics Computer Group, Madison Wis. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%,etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved phannacokinetic properties [see, e.g., EP-A 0232 262]. On the other hand, for some uses it would be desirable to be able to delete the Fc part after the fusion protein has been expressed, detected and purified.

All publications, including but not limited to patents and patent applications, cited in this specification are herein incorporated by reference as if each individual publication were specifically and individually indicated to be incorporated by reference herein as though fully set forth.

What is claimed is:

1. An isolated polynucleotide which comprises the nucleotide sequence of SEQ ID NO: 1.

2. An isolated polynucleotide of claim 1 which consists of the nucleotide sequence of SEQ ID NO: 1.

3. An isolated polynucleotide comprising a nucleotide sequence encoding a polypeptide comprising the amino acid sequence of SEQ ID NO:2.

4. The isolated polynucleotide of claim 3 which is DNA.

5. The isolated polynucleotide of claim 3 which is RNA.

6. An isolated polynucleotide comprising nucleotides 156 to 7688 of the nucleotide sequence of SEQ ID NO:1.

7. An isolated polynucleotide comprising a polynucleotide sequence which is fully complementary to a nucleotide sequence encoding the amino acid sequence of SEQ ID NO:2.

8. The isolated polynucleotide of claim 7 wherein said polynucleotide sequence is fully complementary to nucleotides 156 to 7688 of the nucleotide sequence of SEQ ID NO:1.

9. An expression system comprising a polynucleotide capable of producing a polypeptide comprising the amino acid sequence of SEQ ID NO:2.

10. A process for producing a recombinant host cell comprising transforming or transfecting a host cell in vitro with the expression system of claim 9 such that the host cell produces said polypeptide in vitro.

11. A recombinant host cell produced by the process of claim 10.

12. A cell membrane of a recombinant host cell of claim 11 expressing said polypeptide.

13. A process for producing a polypeptide comprising culturing a recombinant host cell of claim 10 under conditions sufficient for the production of said polypeptide and recovering said polypeptide from the culture.

* * * * *